(12) United States Patent
Alayad

(10) Patent No.: US 10,092,372 B1
(45) Date of Patent: Oct. 9, 2018

(54) ELASTICALLY TENSIONED DENTAL MATRIX WEDGE

(71) Applicant: KING SAUD UNIVERSITY, Riyadh (SA)

(72) Inventor: Abdullah Saeed M. Alayad, Riyadh (SA)

(73) Assignee: KING SAUD UNIVERSITY, Riyadh (SA)

(*) Notice: Subject to any disclaimer, the term of this patent is extended or adjusted under 35 U.S.C. 154(b) by 0 days.

(21) Appl. No.: 15/944,739

(22) Filed: Apr. 3, 2018

(51) Int. Cl.
*A61C 5/88* (2017.01)
*A61C 5/85* (2017.01)
*A61C 8/00* (2006.01)
*A61C 8/02* (2006.01)

(52) U.S. Cl.
CPC .............. *A61C 5/88* (2017.02); *A61C 8/0089* (2013.01); *A61C 5/85* (2017.02); *A61C 8/0006* (2013.01)

(58) Field of Classification Search
CPC .... A61C 5/80; A61C 5/82; A61C 5/88; A61C 5/85; A61C 8/0089; A61C 8/0006; A61C 7/02; A61C 7/146
USPC .................................................. 606/151–158
See application file for complete search history.

(56) References Cited

U.S. PATENT DOCUMENTS

| | | | |
|---|---|---|---|
| 819,136 A | 5/1906 | Herman | |
| 3,262,208 A * | 7/1966 | Johnson, Jr. | A61C 5/85 433/39 |
| 4,259,070 A | 3/1981 | Soelberg et al. | |
| 4,303,389 A * | 12/1981 | Salsarulo | A61C 5/85 433/40 |
| 4,696,646 A | 9/1987 | Maitland | |
| 4,715,816 A | 12/1987 | Mogelof | |
| 6,234,793 B1 | 5/2001 | Brattesani et al. | |
| 8,224,485 B2 * | 7/2012 | Unsworth | B25J 9/06 700/245 |
| 9,138,133 B2 * | 9/2015 | Breedveld | A61B 1/0055 |
| 2002/0081552 A1 | 6/2002 | Stanwich et al. | |
| 2003/0186194 A1 | 10/2003 | Corti | |
| 2004/0146838 A1 * | 7/2004 | Nugiel | A61C 5/00 433/226 |
| 2011/0306007 A1 | 12/2011 | Ericson et al. | |
| 2013/0344455 A1 * | 12/2013 | Hull | A61C 5/125 433/29 |
| 2016/0100901 A1 | 4/2016 | Zaakhary | |

* cited by examiner

*Primary Examiner* — Edward Moran
*Assistant Examiner* — Drew Folgmann
(74) *Attorney, Agent, or Firm* — Richard C. Litman

(57) ABSTRACT

The elastically tensioned dental matrix wedge is a dental matrix wedge for use in dental restoration procedures. The elastically tensioned dental matrix wedge includes a hollow elongated body having first and second longitudinally opposed ends. The first end is at least partially open and the second end is closed. An elongated tube is mounted within the hollow elongated body and extends longitudinally therein. A spiral torsion spring is secured to, and wraps about, the elongated tube. A clip is provided for releasably holding the spiral torsion spring in a compressed state. Release of the clip allows the spiral torsion spring to expand and exert an elastic tension force on an inner surface of the hollow elongated body.

6 Claims, 3 Drawing Sheets

ELASTICALLY TENSIONED DENTAL MATRIX WEDGE

BACKGROUND

1. Field

The disclosure of the present patent application relates to dental restorations, and particularly to an elastically tensioned dental matrix wedge for use during dental restoration procedures.

2. Description of the Related Art

A dental restoration or dental filling is a treatment to restore the function, integrity, and morphology of missing tooth structure resulting from caries or external trauma. As shown in FIG. 3, a typical matrix system for dental restoration includes a matrix M, or matrix band, as well as a wedge W, and possibly a separate matrix retainer. FIG. 3 illustrates a conventional prior art matrix system in use in a restoration of a cavity in tooth $T_2$. Matrix M is placed between teeth $T_1$ and $T_2$, as shown. In FIG. 3, the dentist has shaped tooth $T_2$, by forming recess R, to receive dental filling material FM. To ensure that the hardened filling material FM, whether of the amalgam or composite resin type, is of the correct shape (i.e., ensuring proper contact between the cavity-containing tooth $T_2$ and its neighbors), matrix M forms a wall or barrier to prevent dental filling material FM from deforming into an unwanted shape before it hardens.

In order to aid in the separation and approximate the gingival portion of tooth $T_2$ during the dental restoration process, as well as stabilizing matrix M, a wedge W is placed in the interproximal area, as shown in FIG. 3. As shown, matrix M, stabilized by wedge W, will prevent the flowing of the dental filling material FM beyond the gingival margin of tooth $T_2$. FIG. 2 illustrates such a conventional dental matrix wedge W. As shown, dental matrix wedge W is elongated and includes a gripping or grasping portion G, as well as an engaging portion E. As shown, gripping or grasping portion G typically includes a pair of side grooves, providing an easily graspable surface for the dentist's fingers. Engaging portion E has a substantially triangular cross-sectional contour, as shown, for being received between teeth $T_1$ and teeth $T_2$, as seen in FIG. 3. The gripping or grasping portion G is typically wider than the engaging portion E, providing an easily gripped surface for the dentist to hold, particularly by using the pair of side grooves shown in FIG. 2.

The wedge W may be formed from an elastomeric material or, commonly, from an absorbent material, such as wood. Such interproximal wedges, however, are often cumbersome, particularly when used in between teeth with tight contact. Such wedges are also known to displace the gingival papilla, resulting in pain, irritation and gingival bleeding. It would obviously be desirable to provide a dental matrix wedge which is easily and comfortably insertable and removable. Thus, an elastically tensioned dental matrix wedge solving the aforementioned problems is desired.

SUMMARY

The elastically tensioned dental matrix wedge is a dental matrix wedge for use in dental restoration procedures. The elastically tensioned dental matrix wedge includes a hollow elongated body having first and second longitudinally opposed ends. The first end is at least partially open and the second end is closed. An elongated tube is mounted within the hollow elongated body and extends longitudinally therein. A spiral torsion spring is secured to, and wraps about, the elongated tube. A clip is provided for releasably holding the spiral torsion spring in a compressed state. Release of the clip allows the spiral torsion spring to expand and exert an elastic tension force on an inner surface of the hollow elongated body.

In use, a dental matrix is positioned between a tooth to be restored and an adjacent tooth. An engaging portion of the elastically tensioned dental matrix wedge is then inserted between the dental matrix and the tooth to be restored. Initially, the spiral torsion spring is held in its compressed state by the clip. Once the elastically tensioned dental matrix wedge is fully positioned between the dental matrix and the tooth to be restored, with the elastically tensioned dental matrix wedge positioned adjacent the gingiva of the patient, the clip is released, causing the spiral torsion spring to expand. Expansion of the spiral torsion spring exerts an elastic tension force on an inner surface of the hollow elongated body and causes the elongated body to expand as much as necessary to fill an available space or gap. In this manner, the wedge can firmly secure the dental matrix in place.

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
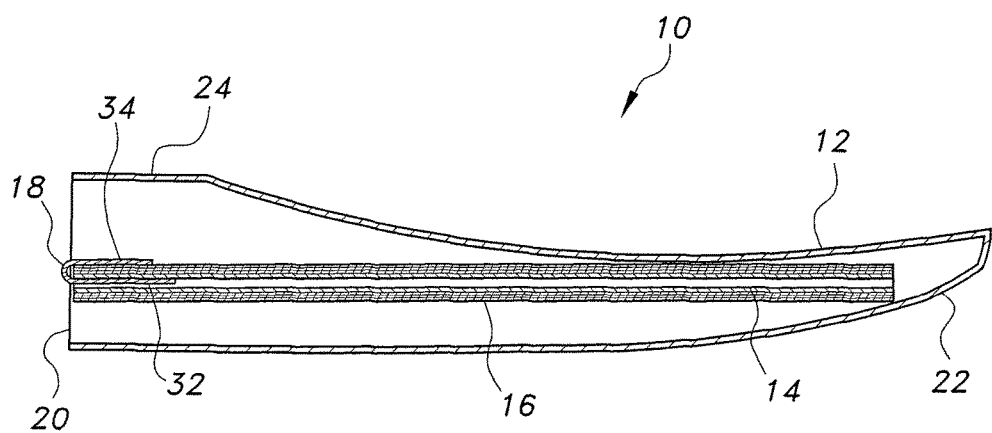
FIG. 1 is a side view in section of an elastically tensioned dental matrix wedge.
Figure 2:
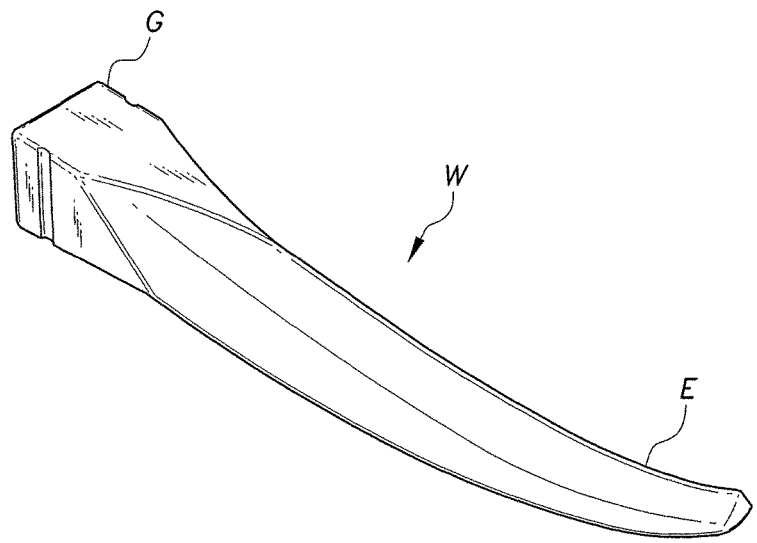
FIG. 2 is a perspective view of a conventional prior art dental matrix wedge.

The elastically tensioned dental matrix wedge 10 is a dental matrix wedge for use in dental restoration procedures, such as those described above with respect to FIGS. 2 and 3. As shown in FIG. 1, the elastically tensioned dental matrix wedge 10 includes a hollow elongated body 12 having first and second longitudinally opposed ends 20, 22, respectively. The first end 20 is at least partially open and the second end 22 is closed. The hollow elongated body 12 has a gripping portion 24 formed adjacent the first end 20, which is adapted for gripping or grasping by the dentist. The hollow elongated body 12 further has an engaging portion 26 extending between the gripping portion 24 and the second end 22. The engaging portion 26 is tapered from the gripping portion 24 to the second end 22, allowing for ease of insertion between adjacent teeth during the dental restoration procedure. It should be understood that the overall contouring and relative dimensions of the hollow elongated body 12 are shown for exemplary purposes only. It should be further understood that hollow elongated body 12 may be made from any suitable type of elastomeric material or the like.

Figure 4:
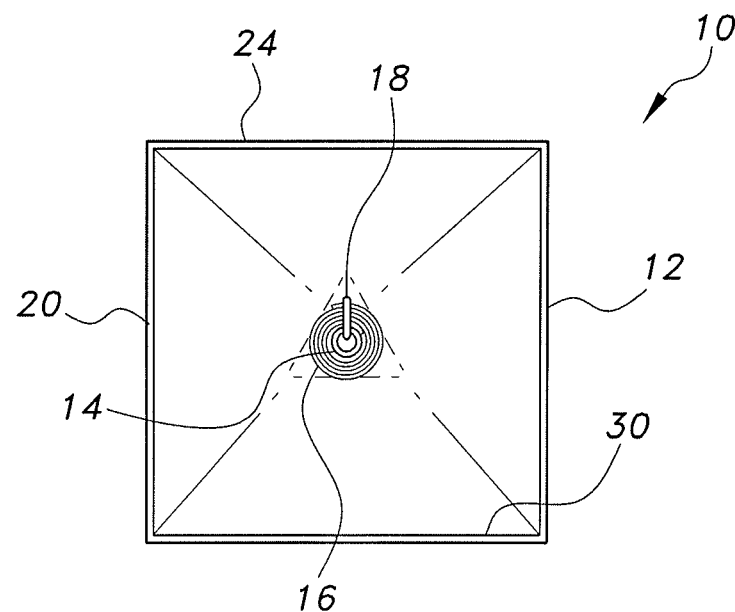
FIG. 4 is a rear view of the elastically tensioned dental matrix wedge showing a spiral torsion spring thereof in a compressed state.
Figure 5:
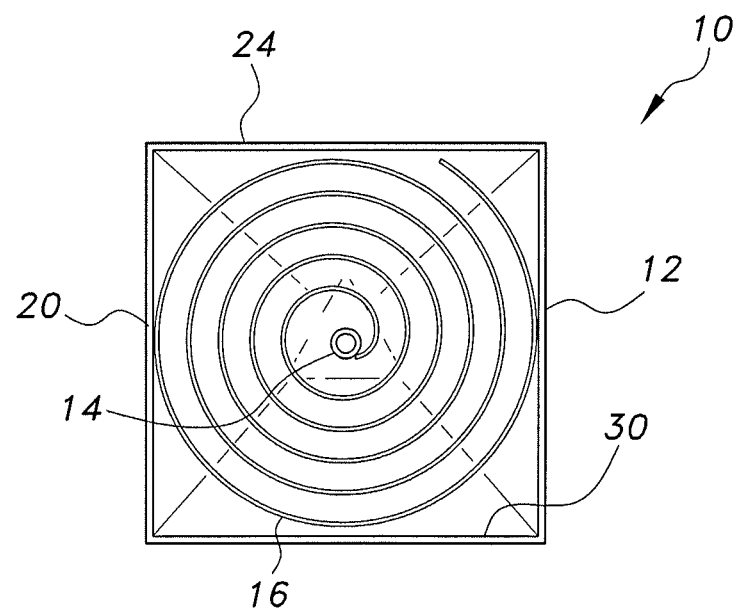
FIG. 5 is a rear view of the elastically tensioned dental matrix wedge showing the spiral torsion spring in an expanded state.

An elongated tube 14 is mounted within the hollow elongated body 12 and extends longitudinally therein. A spiral torsion spring 16 is secured to, and wraps about, the elongated tube 14. In FIGS. 1 and 4, the spiral torsion spring 16 is shown in a tightly wound, or compressed, state. As shown, a clip 18 is provided for releasably holding the spiral torsion spring 16 in this compressed state. Release of the clip 18 allows the spiral torsion spring 16 to expand and exert an elastic tension force on inner surface 30 of the hollow elongated body 12, as shown in FIG. 5. It should be understood that clip 18 is shown for exemplary purposes only. In this non-limiting example, clip 18 is similar to a bobby pin, with a first arm 32 inserted within the elongated tube 14, and with a second arm 34 adapted for releasably holding a portion of the spiral torsion spring 16 against an exterior of the elongated tube 14. However, it should be understood that any suitable type of clip, clasp or the like may be used to releasably hold the spiral torsion spring 16 in the compressed state.

Figure 3:
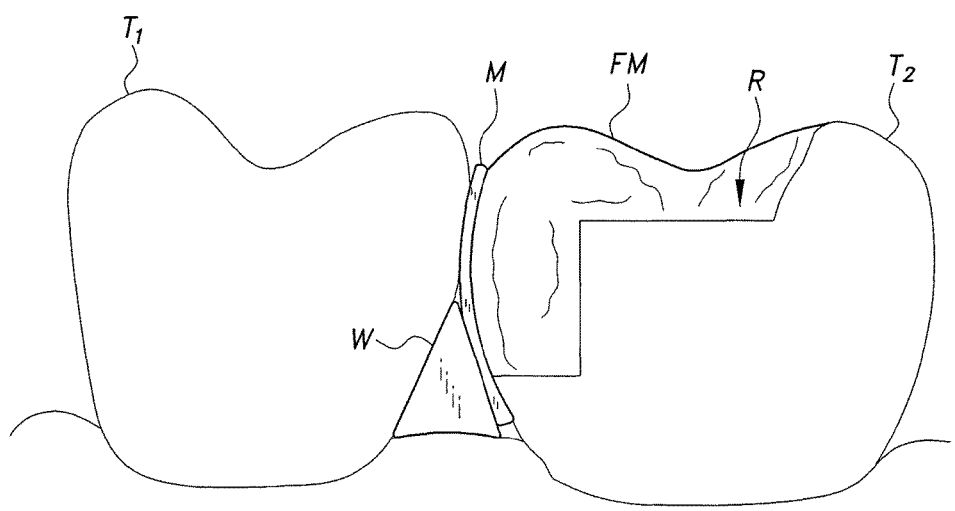
FIG. 3 illustrates a conventional dental restoration procedure using the prior art dental matrix wedge of FIG. 2.

In use, a dental matrix is positioned between a tooth to be restored and an adjacent tooth, similar to dental matrix M being positioned between teeth $T_1$ and $T_2$ in FIG. 3. The engaging portion 26 of the elastically tensioned dental matrix wedge 10 is then inserted between the dental matrix M and the tooth to be restored $T_2$. Initially, the spiral torsion spring 16 is held in its compressed state by the clip 18, as in FIGS. 1 and 4. Once the elastically tensioned dental matrix wedge 10 is fully positioned between the dental matrix M and the tooth to be restored $T_2$, with the elastically tensioned dental matrix wedge 10 positioned adjacent the gingiva of the patient, the clip 18 is released, causing the spiral torsion spring 16 to expand, as in FIG. 5. Expansion of the spiral torsion spring 16 exerts an elastic tension force on the inner surface 30 of the hollow elongated body 12 and causes the elongated body to expand as much as necessary to fill an available space or gap. In this manner, the wedge 10 can firmly secure the dental matrix M in place. The expandable nature of the elastically tensioned dental matrix wedge 10 allows such wedges 10 to be manufactured in a single size, regardless of the size of the proximal cavity. Thus, both time and manufacturing costs may be saved by removing the choice of proper size, as in conventional matrix wedges, through the usage of wedge 10, manufactured in one standard size, which can expand to fill the interproximal space.

It is to be understood that the elastically tensioned dental matrix wedge is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. An elastically tensioned dental matrix wedge, comprising:
   a hollow elongated body having first and second longitudinally opposed ends, the first end thereof being at least partially open and the second end being closed;
   an elongated tube mounted within the hollow elongated body and extending longitudinally therein;
   a spiral torsion spring secured to, and wrapped about, the elongated tube; and
   a clip for releasably holding the spiral torsion spring in a compressed state, wherein release of the clip allows the spiral torsion spring to expand and exert an elastic tension force on an inner surface of the hollow elongated body, wherein the elastically tensioned dental matrix wedge is configured to be inserted into an interproximal space between a dental matrix band and a tooth, and secured therebetween by action of the elastic tension force.

2. The elastically tensioned dental matrix wedge as recited in claim 1, wherein the hollow elongated body has a gripping portion formed adjacent the first end and an engaging portion extending between the gripping portion and the second end, the gripping portion being wider than the engaging portion.

3. The elastically tensioned dental matrix wedge as recited in claim 2, wherein the engaging portion has a substantially triangular cross-sectional contour.

4. The elastically tensioned dental matrix wedge as recited in claim 3, wherein the engaging portion is tapered from the gripping portion to the second end.

5. The elastically tensioned dental matrix wedge as recited in claim 1, wherein the clip has first and second arms, the first arm thereof being removably received within the tube, the second arm thereof releasably holding a portion of the spiral torsion spring against an exterior of the elongated tube.

6. A method of securing a dental matrix, comprising the steps of:
   positioning a dental matrix band between a tooth to be restored and an adjacent tooth;
   inserting at least a portion of an elastically tensioned dental matrix wedge between the dental matrix band and the adjacent tooth, below a cavity gingival margin thereof, the elastically tensioned dental matrix wedge having a spiral torsion spring mounted within a hollow elongated body of the elastically tensioned dental matrix wedge, the spiral torsion spring being releasably held in a compressed state within the hollow elongated body by a clip; and
   releasing the clip such that the spiral torsion spring expands to exert an elastic tension force on an inner surface of the hollow elongated body.

* * * * *